United States Patent [19]
Banks

[11] Patent Number: 6,131,208
[45] Date of Patent: Oct. 17, 2000

[54] EYE PROTECTION APPARATUS AND METHOD

[75] Inventor: Gary Banks, Herts, United Kingdom

[73] Assignee: World Suncare Products, Ltd., Herts, United Kingdom

[21] Appl. No.: 09/186,862

[22] Filed: Nov. 5, 1998

[51] Int. Cl.[7] ........................................ A61F 9/02
[52] U.S. Cl. .................. 2/432; 128/858; 351/110
[58] Field of Search ................... 2/15, 426, 432, 2/431; 128/858; 351/41, 110, 47

[56] References Cited

U.S. PATENT DOCUMENTS 2,572,638  10/1951  Loos ............................................ 2/15 X
4,162,542   7/1979  Frank ............................................ 2/15

*Primary Examiner*—Peter Nerbun
*Attorney, Agent, or Firm*—Elliott N. Kramsky

[57] ABSTRACT

Eye protection is disclosed comprising a generally domed eye protector having a base and being shaped to fit over a single eye, and an attachment structure, comprising a double-sided adhesive portion of a shape corresponding to the base, an upper, releasable cover sheet and a layer release layer. The upper and lower releasable layers are removed from the adhesive layer, which is used to affix the eye protector over a user's eye.

The invention is of particular use for eye protection during the use of a tanning bed, sunbed or other tanning apparatus.

6 Claims, 2 Drawing Sheets

EYE PROTECTION APPARATUS AND METHOD

BACKGROUND OF THE INVENTION

This invention relates to eye protection. In particular it relates to an eye protection device and a method for affixing an eye protection device to an eye, particularly for use when a wearer is using a sun lamp, sunbed, tanning bed or other skin tanning apparatus.

Eye protection for use with sun lamp has in the past generally comprised ultraviolet blocking goggles with nose bridges and/or elastic headband fastening. However, the nature of these means that they extend over a larger area than the area of the eye and so the use may run the risk of tanning his face by virtue of the sun lamp, except for an untanned area around the eyes, which can look strange and is undesirable. Accordingly, more recently, attempts have been made to provide eye protection which fits directly over the eyes and thus allows more of the skin surface to be tanned. One-piece type of eye protectors are usually intended to be disposable and can only be used once.

Up to now, this type of eye protection has been merely placed upon the areas directly around the eyes and the user lies down while wearing the devices. While the devices do, to a certain extent keep in position with respect to the eye with small movements of the An object of the present invention is to provide an improved method of attaching an eye protector of the individual eye covering type, to the eye.

A further object of the present invention is to provide an improved, preferably low cost, protection system that allows maximum tanning but is reusable.

SUMMARY OF THE INVENTION

According to the present invention there is provided, in combination, an eye

Protector in the form of a generally domed structure arranged to fit over the eye and eyelid, and an attachment structure, comprising a double-sided adhesive portion of a shape corresponding to the base of the eye protector, an upper releasable cover sheet and a lower release layer.

The invention also provides a method of attaching an eye protector as described over an eye, comprising removing the upper layer sheet to expose a first adhesive layer of the adhesive portion; affixing said eye protector to the adhesive portion; removing the lower sheet to expose a second adhesive layer and attaching the eye protector, by means of the adhesive portion, to the area around a user's eye.

The terms 'upper', and 'lower' are not to be construed as limiting the disposition of apparatus according to the invention.

DESCRIPTION OF THE DRAWINGS

Embodiments of the invention will now be described, by way of example only, with reference to the accompanying drawings, in which.

DESCRIPTION OF PREFERRED EMBODIMENT OF THE INVENTION

Figure 1A:
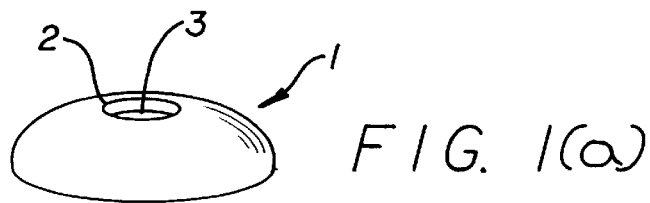
FIG. 1(a) shows an eye protector.
Figure 1B:
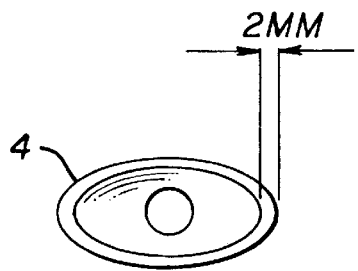
FIG. 1(b) shows an underplan view of the protector assembly.

Referring to FIG. 1, an eye protector 1 is shaped to be applied over a single eye and to contact the region directly around the eye, including the eyelids. The eye protector 1 has a generally oval base 4 of maximum length approximately 3.8 cm and maximum width approximately 2.5 cm. The base surface has a width of about 2 mm. The eye protector is generally domed as shown in FIG. 1(a) and is of a plastics material, preferably a rigid plastics material such as ABS. It is provided, at its top surface, with a generally circular aperture 2 which includes a lip for supporting a lens 3 of a tinted plastics or other optical material which blocks UVA and UVB light. Thus, the article is shaped and designed so that it can be fitted over an eye to substantially prevent ultraviolet radiation from entering the eye and possibly damaging the eye, while still allowing a degree of vision to the user through lens 3. Lens 3 preferably has no optical power although of course it, may have optical power where necessary.

In use a pair of protectors 1 will be provided such that one of them is applied over each eye.

Figure 2A:
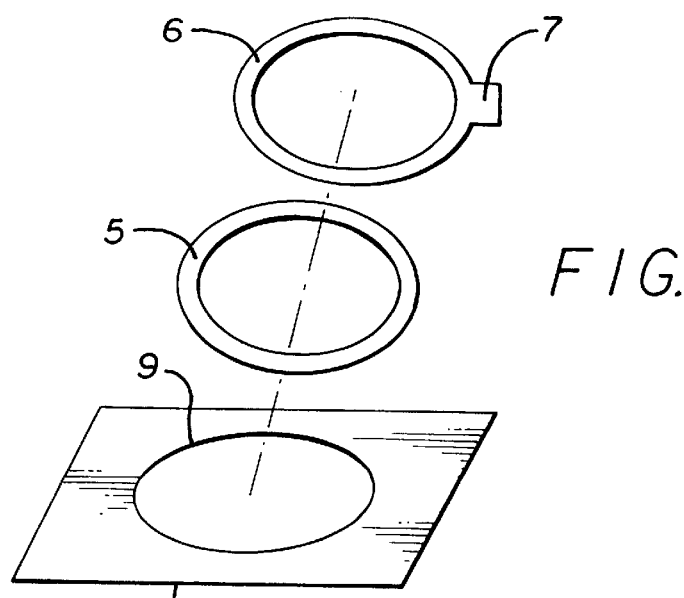
FIG. 2(a) shows an exploded view of the components of an affixing sheet.
Figure 2B:
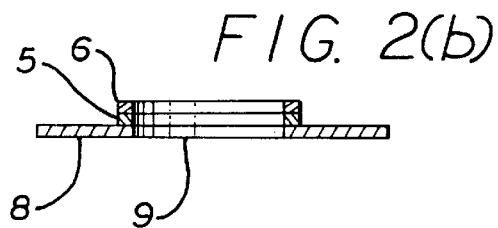
FIG. 2(b) shows a cross-section through an affixing assembly.

FIGS. 2(a) and 2(b) show a structure including an adhesive layer for allowing attachment of an eye protector to the area around the user's eye. FIG. 2(a) shows an exploded view of the various components and FIG. 2(b) shows a cross-sectional view of the resulting sandwich construction in which the relative depth has been exaggerated for clarity.

The attachment structure comprises a generally oval attachment member 5 which is of substantially the same dimensions as the hollow base 4 of the domed eye protector 1. Member 5 is of a flexible plastics material and is coated with an adhesive on both faces thereof That is, it is a doublesided adhesive layer or gasket. The adhesive is preferably a medical grade adhesive material of a type which causes secure adhesion of a material onto the skin but which is relatively easily and relatively painlessly removed from the skin when necessary. It may thus be a type of adhesive which is used for sticking plasters, and other wound dressing type materials and as such many different adhesive of this type are well known in the art. It should also preferably be of a type which is substantially non-allergenic so as not to cause irritation of the skin against such contacts.

A first removable layer 6 is applied above double adhesive layers 5 and this is a removable top cover layer which has a non-adhesive surface. It is generally oval in shape, of similar proportions and size to adhesive layer 5 but may also include a means such as tab 7 for easily removing layer 6 relative to layer 5. Since tab 7 will not lie in contact with an adhesive part of layer 5, it will be easy in use to simply lift tab 5 and lift the whole of cover part 6 off to release it, leaving the adhesive top layer of part 5 exposed.

Underneath part 5 there is provided a further release sheet 8 which may be generally rectangular as shown or may be of other shapes. This may be unbroken or may, in some embodiments, include a central aperture 9 which is generally oval in shape and of generally similar dimensions to the inner surface of double adhesive layer 5 (and thereby the inner surface of base 4 of eye protector 1). Substrate 8 is of a flexible material which again serves as a release layer against double-sided layer 5 and can be removed therefrom so that, when both layers 6 and 8 are removed, both adhesive surfaces of layer 5 are exposed.

The upper and lower release layers may of course be of sizes and shapes different to those of the preferred embodiment. Layer 6 for example may be rectangular, circular or otherwise shaped.

Figure 3:
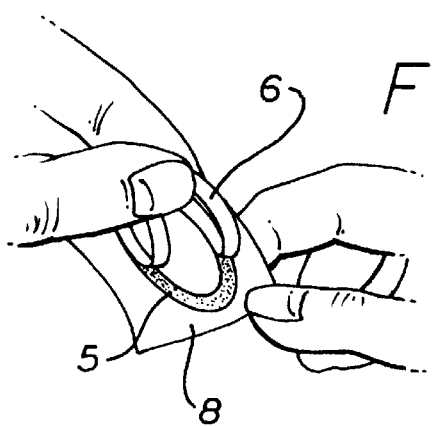
FIG. 3 to 6 show respective steps for affixing the eye protector to an eye.
Figure 4:
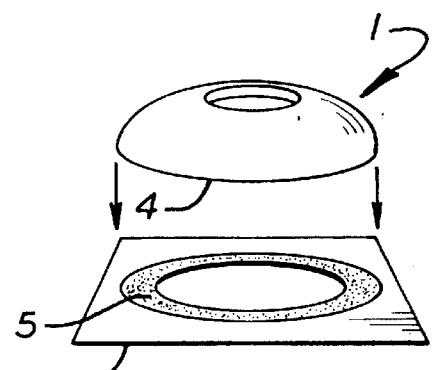

FIGS. 3 to 6 show an example of the manner in which an attachment structure 5 to 8 is used to attach an eye protector to an eye. Firstly, layer 6 is peeled away from the sandwich structure, leaving the adhesive to face of layer 5 exposed (FIG. 3).

The next step, (of FIG. 4) is to place one of the eye protectors over, and in register with, part 5. The exposed adhesive top layer of part 5 will cause the eye protector to adhere, along the extent of its base 4, to this layer. In order to facilitate this, and facilitate registration of the eye protector with the adhesive layer, layer 5 is preferably colored so as to distinguish it from layer 8, which is preferably transparent. However, other distinctions may be used and top covering layer 6 may also be colored or otherwise have a different appearance as desired. Layer 8 may alternatively have a colored or otherwise distinguished portion which enables easy registration.

When the layer 8 has a central aperture, this may be used to line up the eye protector by feeling for the aperture with fingers.

Figure 5:
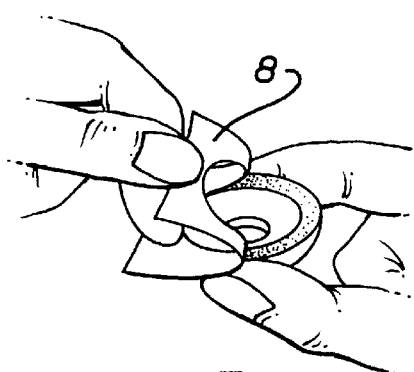

With the sandwich thus adhered to the base of the eye protector, the bottom layer 8 is removed by generally peeling this away. Layer 8 is made of a release material such that the adhesion between adhesive layer 5 and the base of the eye protector is greater than the adhesion between layer 5 and layer 8, causing layer 8 to preferentially be removed when this is peeled away, as shown in FIG. 5. This exposes the other adhesive face of layer 5. Effectively, the eye protector now has an adhesive layer on its base.

Figure 6:
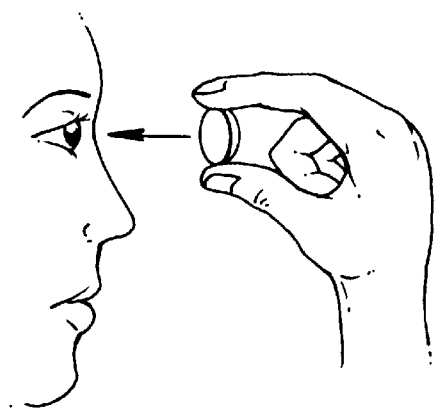

Finally, as shown in FIG. 6, the eye protector is placed in position around a user's eye and the adhesive bottom pan of layer 5 causes the protector to be adhesively secured to the area around the eye. The shape of the eye protector enables a good seal against undesired UV radiation and the user still has visibility out of lens part 3.

After use, the protector is simply peeled off the skin and may simply be discarded. Preferably, however, the protector may be re-used. For example, the adhesive layer 5 may be removed from the base of the protector. This may be facilitated by using medical grade adhesive which is capable of lifting from the protector surface (and skin surface) when necessary. Such adhesives are well known per se. The protector can then be reused many times by reapplying a new attachment structure for each use; Alternatively, the adhesive layer may remain in place between uses.

What is claimed is:

1. Eye protection apparatus comprising a generally domed eye protector arranged to fit over the eye and eyelid and having an annular-base in combination with an attachment structure for contacting the eyelid, said attachment structure comprising a double-sided adhesive portion of a shape corresponding to the base of the eye protector, an upper removable sheet covering a first adhesive layer and a lower removable sheet covering a second adhesive layer.

2. Eye protector as claimed in claim 1, wherein the upper layer has at least a portion of similar shape to the adhesive portion.

3. Eye Protector as claimed in claim 1, wherein the aperture of the lower release layer has an aperture of substantially identical shape to the inner surface of the base of the eye protector.

4. Eye protector as claimed in claim 1, wherein the eye protector is provided with a lens portion which allows visibility therethrough, while providing protection against undesired radiation.

5. Eye Protector as claimed in claim 2, wherein the upper cover layer is provided with one or more release tabs.

6. A method of affixing the eye protector of claim 1 comprising:
   a) removing an upper sheet of an attachment structure to expose a first adhesive layer of an adhesive portion;
   b) affixing said eve protector to said first adhesive portion;
   c) removing a lower sheet of an attachment structure to expose a second adhesive layer; and
   d) attaching the eye protector to an eye by means of said second adhesive layer.

* * * * *